(12) United States Patent
Pidcock et al.

(10) Patent No.: US 9,239,302 B2
(45) Date of Patent: Jan. 19, 2016

(54) METHOD AND APPARATUS FOR ANALYSING A MATERIAL

(75) Inventors: Andrea Gabrielle Pidcock, Melbourne (AU); Robin Greenwood-Smith, Mt. Martha (AU); Trevor Heuer, Mindarie (AU)

(73) Assignee: Technological Resources Pty. Limited, Melbourne (AU)

( * ) Notice: Subject to any disclaimer, the term of this patent is extended or adjusted under 35 U.S.C. 154(b) by 1237 days.

(21) Appl. No.: 13/062,880

(22) PCT Filed: Sep. 8, 2009

(86) PCT No.: PCT/AU2009/001179
§ 371 (c)(1),
(2), (4) Date: Aug. 10, 2011

(87) PCT Pub. No.: WO2010/025528
PCT Pub. Date: Mar. 11, 2010

(65) Prior Publication Data
US 2011/0288787 A1   Nov. 24, 2011

(30) Foreign Application Priority Data
Sep. 8, 2008   (AU) .................................. 2008904660

(51) Int. Cl.
| G01N 1/02 | (2006.01) |
| G01N 1/04 | (2006.01) |
| G01N 1/08 | (2006.01) |
| G06F 3/01 | (2006.01) |
| G01N 23/087 | (2006.01) |
| G01N 33/22 | (2006.01) |

(52) U.S. Cl.
CPC .............. *G01N 23/087* (2013.01); *G01N 33/22* (2013.01)

(58) Field of Classification Search
CPC ........................................................ G01N 1/02
USPC ...................... 702/23, 28, 32, 179, 194, 196; 250/358.1; 378/55, 57; 382/141; 700/223
See application file for complete search history.

(56) References Cited

U.S. PATENT DOCUMENTS

| 5,060,249 A | * | 10/1991 | Eisen et al. ...................... 378/57 |
| 5,204,889 A | * | 4/1993 | Kraybill .......................... 378/54 |
| 6,122,343 A | * | 9/2000 | Pidcock ........................... 378/53 |
| 6,449,334 B1 | * | 9/2002 | Mazess et al. ................... 378/53 |

(Continued)

FOREIGN PATENT DOCUMENTS

| EP | 0549 858 B1 | 3/1998 |
| WO | WO 2008/017075 A2 | 2/2008 |

OTHER PUBLICATIONS

International Search Report from the Australian Patent Office for International Application No. PCT/AU2009/001179 (Mail date Nov. 16, 2009).

(Continued)

*Primary Examiner* — John Breene
*Assistant Examiner* — Felix Suarez
(74) *Attorney, Agent, or Firm* — Banner & Witcoff, Ltd.

(57) ABSTRACT

A method of analyzing particles of a material which include a constituent is disclosed. The method comprises the steps of exposing particles of the material to x radiation having a range of x-radiation energies, detecting x-radiation intensities at two different energy levels transmitted through the particles, and determining the concentration of the constituent in particles from the detected intensities.

16 Claims, 5 Drawing Sheets

(56) References Cited

U.S. PATENT DOCUMENTS

| | | | |
|---|---|---|---|
| 7,696,480 B2* | 4/2010 | Kostka et al. | 250/358.1 |
| 7,873,201 B2* | 1/2011 | Eilbert et al. | 382/141 |
| 2005/0084069 A1 | 4/2005 | Du et al. | |
| 2007/0030953 A1 | 2/2007 | Sommer, Jr. et al. | |
| 2011/0288679 A1* | 11/2011 | Tavakkoli et al. | 700/223 |

OTHER PUBLICATIONS

Takashi Suzuki et al., "Determination of the Purity of Gold Alloys Using Gamma-Ray Transmission Techniques," Japanese Journal of Applied Physics, vol. 37, No. Part 1, No. 11, Nov. 15, 1998,pp. 6242-6247, XP55004853.

Xu Qi et al., "A novel automated separator based on dual energy gamma-rays transmission; A novel automated sensor," Measurement Science and Technology, vol. 11, Nov. 15, 1998,pp. 1383-1388, XP020063033.

Watt J S et al., "Dual energy gamma-ray transmission techniques applied to on-line analysis in the coal and mineral industries," International Journal of Applied Radiation and Isotops, vol. 36, No. 11, Nov. 1, 1985, pp. 867-877, XPO24626184.

Eslava-Gomez A. and S. J. Parry, "Dual attenuation of X-rays for measurement of the concentration of metals in solution," The Analyst, vol. 127, May 9, 2002, pp. 847-851, XP000002656976.

European Search Report, dated Aug. 30, 2011.

Kehna Khou, Study and Application Progress of X-ray Ore-dressing Method, Jiangxi Metallurgy, vol. 6, No. 1, p. 19, dated Jan. 31, 1986 (No Translation Available).

\* cited by examiner

METHOD AND APPARATUS FOR ANALYSING A MATERIAL

CROSS-REFERENCE TO RELATED APPLICATIONS

The present application is a U.S. National Phase filing of International Application No. PCT/AU2012/001179, filed on Sep. 8, 2009, designating the United States of America and claiming priority to Australian Patent Application No. 2008904660, filed Sep. 8, 2008, and this application claims priority to and the benefit of the above-identified applications, which are both incorporated by reference herein in their entireties.

FIELD OF THE INVENTION

This invention relates generally to a method and an apparatus for analysing a material. The invention has application, although not exclusive application, to determining the concentration of constituents in a material and therefore the economic value of the material. The invention has application, although not exclusive application, to determining the concentration of constituents such as metals in mined ores and therefore the economic value of the ores, such as iron ores.

BACKGROUND OF THE INVENTION

Various methods and devices are available for analysing materials.

The selection of a particular method or device depends on, amongst other requirements, the quantity of the material that may be analysed in a given time.

For example, transmission electron microscopy (TEM) is a valuable tool in materials characterization, but sample analysis is a slow process. Typically, samples of the material must be prepared thin enough to be electron beam transparent. Although a high degree of information may be obtained by TEM analysis, the number of samples that can be prepared and analysed in a single day is very limited. Additionally, the cost of TEM analysis is prohibitive.

High through-put analysis methods and devices are required where large volumes of materials need to be characterized. An example of such an application is waste recycling where glass, for example, needs to be differentiated from metals and plastics.

Another example involves characterizing mined materials. In this regard, one method of analysing particles of as-mined material is disclosed in U.S. Pat. No. 3,655,964 to Slight.

The method involves passing as-mined material through a field of x-radiation at two energy levels in a gap between an x-radiation generating source and a series of x-radiation detectors and determining the intensity of x-radiation that is transmitted through the mined material.

Data on the intensity of transmitted x-radiation at one energy level is obtained at the detectors and is used, in conjunction with a known x-radiation absorption coefficient for a known material, to determine a nominal thickness for the known material. The determined thickness is then used, in conjunction with data obtained at the detectors of transmitted x-radiation at the other energy level, to calculate an x-ray absorption coefficient for the ore. The calculated coefficient is compared against the known coefficient of the known material at the other energy level. If the calculated x-radiation absorption coefficient corresponds with the known coefficient for the known material, the mined material is identified as the known material. If the calculated x-radiation absorption coefficient does not correspond with the known coefficient for the known material, the process is repeated with alternative x-radiation absorption coefficients for other known materials until a match is found.

The claimed advantage of this approach is that the thickness of a particle is removed from consideration in characterizing the material.

The applicant has recognized that the problem with this approach is that the method disclosed in Slight is limited and in practice impossible to implement. Specifically:

1. Slight assumes mono-energy x-radiation beams which in practice are not available or possible, and ignores the impacts of beam hardening and beam scattering which make an accurate assessment of characterization not possible.
2. Use of a pulse height analyser is not possible to operate on particles passing the detector counter at speeds of greater than 1 m/s. Hence, this greatly limits the through-put capacity of the method.
3. The embodied designs of pulsing energy levels from a single energy source, sequentially positioned energy sources or sequentially positioned detection counters do not ensure the same section and orientation of a particle is analysed at each energy level. This introduces analysis errors, and is particularly evident in high speed/high through-put applications as changes in particle position, orientation and trajectory are more pronounced.

In addition, the applicant has recognized that Slight does not disclose how the concentration of constituents of the material can be determined from the analysis method disclosed by Slight.

It is an object of the invention to provide an improved method of analysing materials.

SUMMARY OF THE INVENTION

The invention provides an improved method of analysing materials that makes it possible to determine the concentration of a constituent of the material in applications requiring high speed and high through-put.

Specifically, the applicant has determined that exposing particles of iron ore to x-radiation comprising a range of energies and measuring the intensities of transmitted x-radiation in two or more energy levels or energy ranges enables the concentration of constituent materials in a particle to be determined at high speeds and high through-put capacity. The applicant has also determined that sorting is able to be performed on the basis of constituent concentration within a particle at high speeds and high through-put capacity.

The invention provides a method of analysing particles of a material which include a constituent, the method comprising the steps of:

(a) exposing particles of the material to x-radiation having a range of x-radiation energies;

(b) detecting x-radiation intensities at two different energy levels or at two different ranges of energies transmitted through the particles; and (c) determining the concentration of the constituent occurring in particles from the respective detected intensities.

Based on this method, materials analysis of ores such as iron-containing ores and base and precious metal-containing ores such as copper, nickel, gold, platinum and silver-containing ores is more accurate because errors in calculating grade concentration of ores introduced by variable non-compositional parameters such as thicknesses, porosity, shape and size of ore particles are reduced.

Step (a) of the method of exposing the material to x-radiation may comprise operating the x-radiation source at a voltage of 50 kV to 400 kV.

Step (b) of detecting x-radiation intensities may comprise detecting x-radiation intensities in two different, non-overlapping, ranges of energies.

Step (c) of determining the concentration of the constituent may comprise calculating a parameter, i.e. a value (hereinafter referred to as "value" rather than "parameter") indicative of the concentration of the constituent by performing a numerical operation using the detected intensities at the different energy levels or different energy ranges and at least one constant, with the at least one constant being selected so that an influence of thickness of the material on the calculated value is reduced.

As the detected radiation intensities are associated with respective different energy levels or energy ranges, the intensities typically have different dependencies on the thickness of the material through which the radiation is transmitted. The at least one constant is selected to reduce the influence that variations in non-compositional parameters of particles have on the calculated value and consequently embodiments of the invention have the significant practical advantage that the calculated value, and associated information on the concentration of the material, is of increased accuracy.

The at least one constant may be selected so that the calculated concentration is largely independent of the non-compositional parameters of the material within a thickness range of, say, 5-15 mm, 5-25 mm, 1-25 mm or even 1-50 mm.

The step of calculating the value may comprise forming a ratio of first and second quantities that are associated with detected first and second radiation intensities related to first and second energy levels or first and second energy ranges, thereby reducing the effects of non-compositional parameters, such as particle thickness and porosity, orientation, position and density, on concentration calculations.

One energy range may be a lower energy range and the other energy range may be a higher energy range. The energy ranges may be overlapping ranges. The energy ranges may be non-overlapping ranges.

The method may comprise moving the particles relative to a source of the radiation and a detector for detecting the first and second radiation intensities.

The method may be conducted so that the value is calculated substantially in real time. Consequently, it is then possible to provide information concerning concentration of the constituent substantially in real time.

The calculated value may be indicative of a grade of the ore, such as iron ore grade.

The step of calculating the value may comprise calculating a ratio of a first quantity that is a function of a detected first intensity $I_1$ associated with the first energy level or first energy range and a second quantity that is a function of a detected second intensity $I_2$ associated with the second energy level or second energy range.

The value may be the value of the ratio:

$$\frac{\ln\left(\frac{I_1}{I_{0_1}}\right) + b}{\ln\left(\frac{I_2}{I_{0_2}}\right)^k} \quad \text{Eq. 1}$$

where k is a first constant, b is a second constant and $I_0$ is indicative of a radiation intensity to which the material is exposed.

The method may comprise determining the at least one constant empirically by analyzing thickness, porosity dependency of the first and second intensities for different material compositions, such as ores with different grades.

Determining the at least one constant may comprise numerical operations of displayed data, which may be conducted using a computer routine and may comprise curve fitting procedures.

The step of detecting the first and second intensities may comprise detecting the first and second intensities using respective first and second detector elements.

As in this case the detector elements detect radiation having respective energy ranges, the detector elements may have different sensitivities and the at least one constant may be selected so that the calculated value is largely independent on the different sensitivities of the detector elements.

Step (b) of detecting x-radiation intensities at two different energy levels may comprise making multiple measurements of intensities of transmitted x-radiation through each particle.

The step (a) of exposing particles to x-radiation may comprise conveying the particles at least 5 m/s through a beam of x-radiation. Optionally, the particles may be conveyed at least 7 m/s through the beam of x-radiation.

The step (a) of exposing particles to x-radiation may comprise conveying the particles at a through-put of at least 100 tonnes per hour ("tph"), preferably at least 120 tph, particularly in the case of particles of mined ore having particle sizes of at least 6 mm through the beam of x-radiation.

The method may comprise calculating the value to be accurate to 1% of the concentration of the constituent in the material.

The material may be an ores.

The ore may be, but is not limited to, iron-containing, copper-containing or nickel-containing ore.

The material may be coal.

The material may comprise particles of different shapes, sizes, thicknesses and porosities that are moved relative to the source of radiation and the detector.

The invention also provides a method of processing data associated with a composition of a material, the method comprising:

calculating a value from detected radiation intensities transmitted through substantially the same volume of the material relative to x-radiation detectors to obtain information concerning the composition of the material, the detected radiation intensities being intensities of radiation that are transmitted through the material and being associated with respective different energy levels or energy ranges, and calculating the value further comprising performing a numerical operation using at least one constant selected so that an influence of non-compositional parameters of the material on the calculated value is reduced.

The invention also provides an apparatus for analysing particles of a material which includes a constituent, the apparatus comprising:

(a) a source of x-radiation for producing a beam of x-radiation in at least first and second energy levels or first and second energy ranges;

(b) a detector for detecting x-radiation produced by the source of x-radiation;

(c) conveying means for conveying particles of the material relative to the source of x-radiation such that the particles pass between the source of x-radiation and the detector; and (d) means for determining the concentration of the constituent in each particle from the detected x-radiation at the first and second energy levels or the first and second ranges of energies.

The concentration determining means is adapted to determine the concentration by calculating a value from x-radiation intensities detected by the detector.

The particles may be conveyed at least 5 m/s through the beam of X-radiation. The particles may be conveyed up to at least 7 m/s.

The particles may be conveyed at a through-put of at least 100 tph, preferably at least 120 tph, through the beam of x-radiation.

The concentration determining means may span the width of the conveying means and be capable of independently operating on discrete particles across the width of the conveying means.

The concentration determining means may enable the value to be calculated to be accurate to 1% of the concentration of the valuable material in the ore.

The detector may comprise two arrays of x-radiation sensors with each array being configured to detect x-radiation of a different energy level or different energy range, and each array may be positioned such that the same x-radiation beam that passes through the particle impinges on the corresponding x-radiation sensors in each array.

The detector may comprise two arrays of x-radiation sensors and two filters respectively located between the x-radiation source and the arrays of x-radiation sensors, and with the filters being adapted to enable transmission of x-radiation of different levels of energy or different ranges of energies to the respective arrays.

The invention also provides a computer program for instructing a computer, the computer program being arranged so that, when loaded in the computer, the computer operates in accordance with a method for analysing a composition of a material, the method comprising the steps of:

calculating a value from detected radiation intensities to obtain information concerning the composition of the material, the radiation intensities being intensities of radiation that are transmitted through the material and being associated with respective different energy levels or different ranges of energies, and calculating the value further comprising performing a numerical operation using at least one constant selected so that an influence of non-compositional parameters of the material on the calculated value is reduced.

The at least one constant may be selected so that the calculated value is largely independent of the non-compositional parameters of the material within a thickness range of, say, 5-15 mm, 5-25 mm, 1-25 mm or even 1-50 mm.

Calculating the value may comprise calculating a ratio of first and second quantities that are associated with detected intensities associated with respective first energy and second energy levels or energy ranges.

The material may be an ore, such as an iron-containing ore or a copper-containing ore, and the calculated value may be indicative of a grade of the ore.

The step of calculating the value may comprise calculating a ratio of a first quantity that is a function of a detected first intensity $I_1$ associated with the first energy level or energy range and a second quantity that is a function of a detected second intensity $I_2$ associated with the second energy level or energy range and the at least one constant may be one of two constants.

The value may be the value of the ratio:

$$\frac{\ln\left(\frac{I_1}{I_{0_1}}\right) + b}{\ln\left(\frac{I_2}{I_{0_2}}\right)^k} \qquad \text{Eq. 1}$$

where k is a first selected constant, b is a second selected constant and $I_0$ is indicative of a radiation intensity to which the material is exposed.

The invention also provides a computer which is arranged for receiving instructions from the computer program in accordance with the invention.

BRIEF DESCRIPTION OF THE DRAWINGS

An embodiment of the invention is now described, by way of example only, with reference to the accompanying drawings, in which.

DETAILED DESCRIPTION OF EMBODIMENTS

Embodiments of a method 100 (FIG. 1) and an apparatus 200 (FIGS. 2 and 3) for analysing a composition of a material in accordance with the invention are now described.

The method is described in the context of analysing as-mined iron ore to determine ore grades. However, it will be appreciated that other ores, such as base and precious metal-containing ores such as copper, nickel, gold, platinum and silver-containing ores, and other materials, such as coal, are suitable for composition analysis in accordance with the invention.

The as-mined iron ore is reduced in size by crushing to form particles of iron ore in a range of 5 mm to 50 mm, preferably 6 mm to 35 mm. It is preferable to have a relatively narrow particle size range to improve accuracy of compositional analysis, for example a particle size range of top size being two to three times the bottom size of the range.

Figure 2:
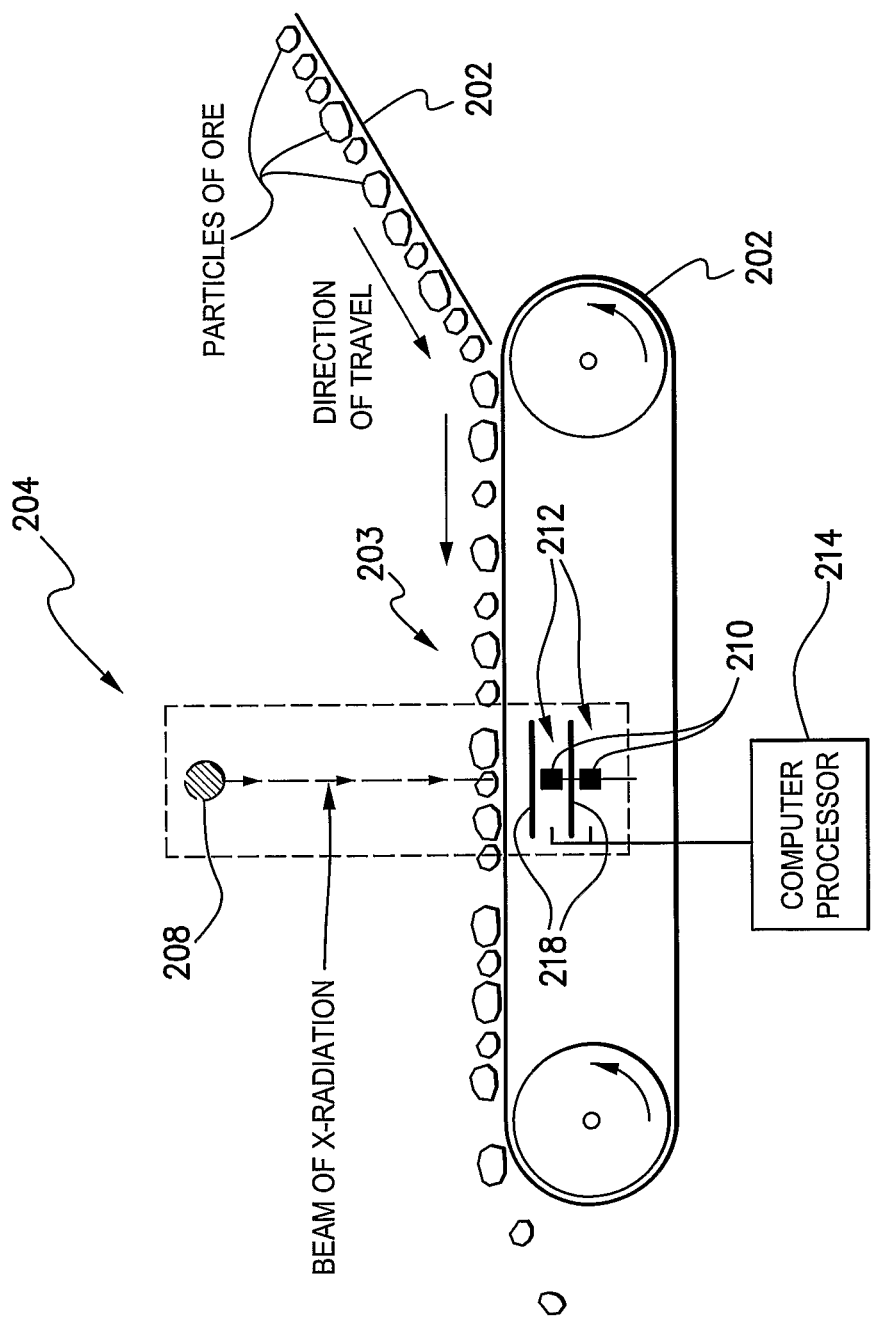
FIG. 2 is a schematic representation of an embodiment of an apparatus for analysing a composition of a material according to the invention.
Figure 3:
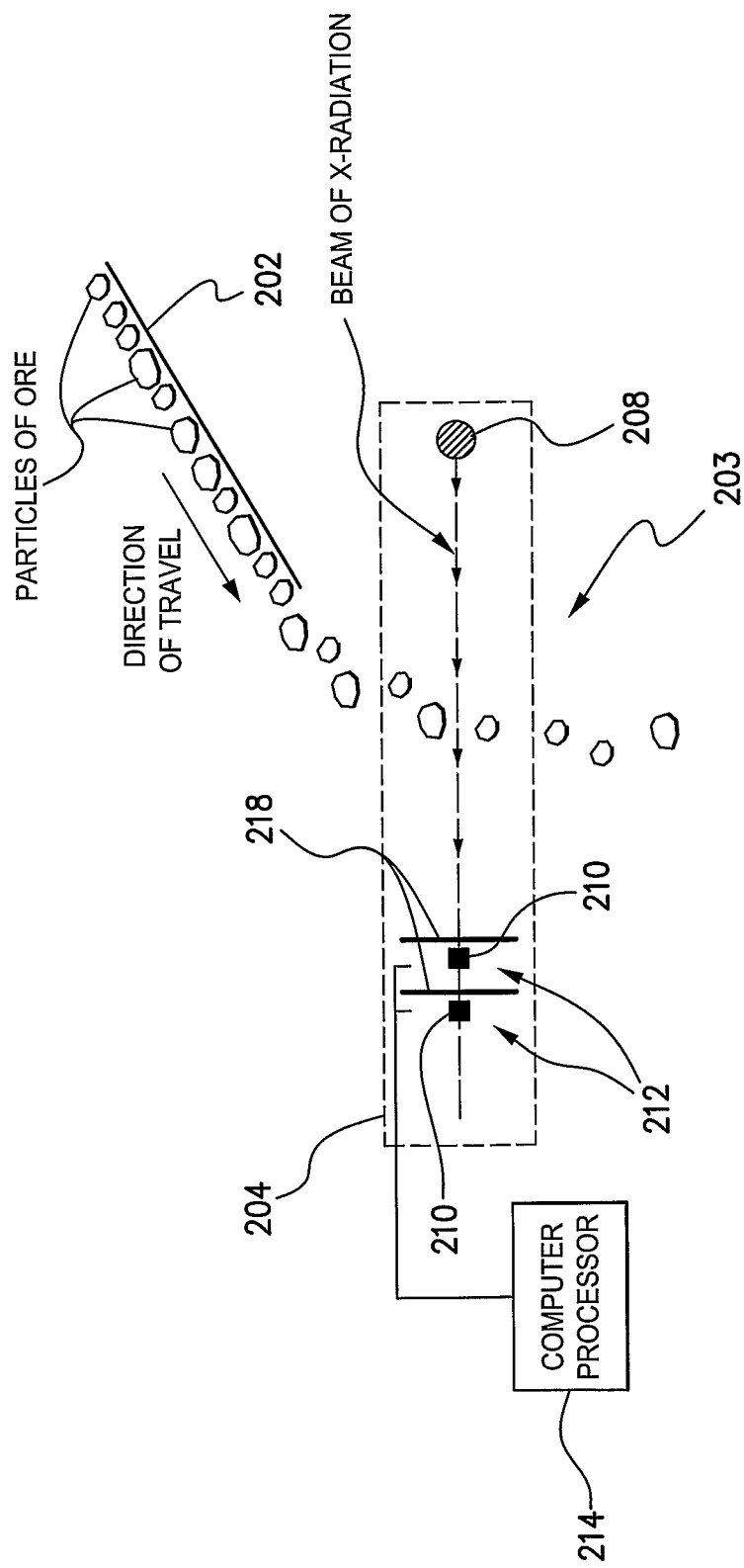
FIG. 3 is a schematic representation of another embodiment of an apparatus for analysing a composition of a material according to the invention.

In both embodiments of the apparatus shown in FIGS. 2 and 3, the ore particles are fed to a conveyor 202 which continuously delivers the iron ore particles in a generally uniform and continuous stream 203 of particles to a concentration determining means in the form of an analysis system 204. It is preferable that the particles in each stream of particles be separated from each other. In the case of the FIG. 2 embodiment it is preferable that the stream of particles be a single particle deep.

The analysis system 204 comprises an x-radiation source 208 positioned on one side of the stream 203 for directing x-radiation through the stream 203 of iron ore particles. X-radiation sensors 210 are positioned on an opposite side of the stream 203 to the x-radiation source 208 so that each sensor 210 simultaneously detects x-radiation transmitted through the same volume of each iron ore particle. The concentration grade assessment of each volume within a particle is used to obtain the concentration grade of the whole particle.

The embodiment shown in FIG. 2 has the analysis system 204 located such that particles travel on a horizontally-extending section of a conveyor belt 202 with the x-radiation source 208 and x-radiation sensors 210 on opposite sides of the conveyor belt 202. The other embodiment shown in FIG. 3 has the analysis system concentration determining means 204 located below a lower end of a slide plate 202 such that particles fall in a trajectory that passes between the x-radiation source 208 and x-radiation sensors 210.

The x-radiation sensors 210 are arranged in two arrays 212 for detecting the intensities of x-radiation that has passed through the particles at two different ranges of x-radiation energies. Specifically, the arrays 212 are arranged with one array above the other array in the case of the FIG. 2 embodiment and one array in front of the other array in the case of the FIG. 3 embodiment such that: (a) x-radiation transmitted through the same volume of each particle is detected at each array 212 and (b) x-radiation of different ranges of energies is detected at each array 212. In each embodiment the upper or front arrays comprise the lower energy sensors 210 and the lower or rearward arrays comprise higher energy sensors 210. Suitable filters 218, such as 1 mm thick silver film filters, are located in front of each array 212 to improve energy separation to facilitate x-radiation of selected ranges of energies (or energy levels) to reach the respective arrays 212. More than two arrays 212 and/or filters 218 may be employed to detect x-radiation intensities of different ranges of x-radiation energies. In both embodiments the arrays 212 of x-radiation sensors 210 extend across the width of the streams 203 of particles.

The apparatus 200 includes a processor 214 that is programmed to calculate compositional information for the iron ore particles based on intensities of x-radiation detected at the x-radiation sensors 210. The x-radiation sensors 210 are linked electronically to the processor 214 for communicating detected x-radiation information to the processor 214. The information is then processed to determine an iron composition grade, i.e. wt. % Fe, of each particle.

Each array 212 comprises multiple sensors 210 in the form of pixels (not shown). The pixel size is selected depending on factors such as the particle size range to be analysed and the speed of movement of the particles. The pixel size may be at least 0.85 mm square. Typically, the pixel size is 1.5 mm square. As such, each pixel is smaller than the smallest sized particle in the nominal particle size range that is fed into the analysis system 204. This enables multiple measurements to be made along the length and across the width of each particle as it traverses the arrays 212. These measurements may be averaged in order to determine the average concentration of a constituent within the particle.

In practice, the iron concentration of each particle is determined from data of multiple measurements of intensities of transmitted x-radiation through each particle by each pixel. In other words, the iron concentration of each particle is based on intensity measurements of multiple discrete volumes through each particle. This is achieved by detecting transmitted x-radiation at multiple times for each pixel exposed to transmitted x-radiation as the particle moves past the pixel. These measurements are taken over the surface of the particle before the "average" iron grade of the particle is calculated by reference to these measurements. This practice involves capturing the multiple detected x-radiation levels at each pixel and using data analysis methodologies, such as image analysis methodologies, to detect and remove edge pixel readings, then using a mean, to get the average iron grade of the particle.

With the apparatus 200 in each of FIGS. 2 and 3 in mind, the method 100 includes a step 102 of exposing a stream 203 of iron ore particles to radiation having a range of energies, with the energies being sufficiently high so that at least a portion of the radiation transmits through the iron ore particles. The x-radiation is provided by the x-radiation source 208, which may be operated at a voltage of 50 to 400 kV, or higher as required. It is preferable that the voltage be in a range of 150-225 Kv. X-radiation generated by the x-radiation source is transmitted through the stream 203 of particles.

The iron ore particles are moved relative to the x-radiation source at a speed up to 7 m/s, typically 5-6 m/sec. Such speeds enable economically viable quantities of iron ore to be analysed according to the invention. While the capacity of the apparatus as measured on an hourly basis depends on stream speed, particle size, and stream width. For example, at least 100 tph of ore can be analysed for particles having a size around 10 mm and with a stream speed of 7 m/s. However, the apparatus 200 will analyse at least 100 to 250 tph of iron ore having particle sizes in a range of 6 mm to 30 mm. In addition, material, such as iron ore, can be analysed at a measured accuracy of 1-3% of material concentration and particularly at capacities of 100 to 250 tph.

Figure 1:
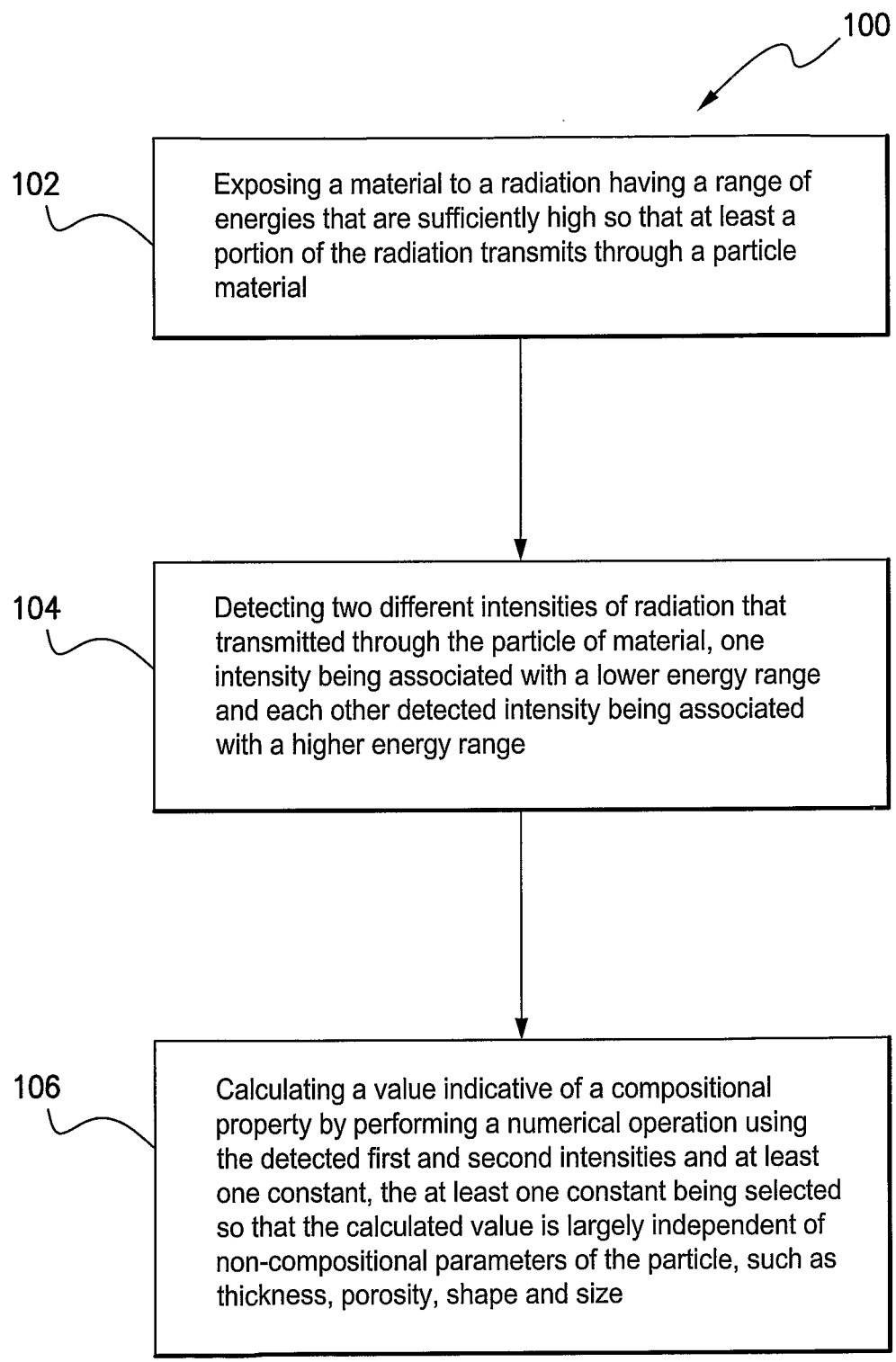
FIG. 1 is a flow chart illustrating one embodiment of a method for analysing a composition of a material according to the invention.

With reference to FIG. 1, and as is evident from the above description of the embodiments of the apparatus shown in FIGS. 2 and 3, the method 100 also includes a step 104 of detecting first and second intensities of radiation that are transmitted though the material at two different energy ranges (or energy levels). The first intensity is associated with a lower energy range and the second intensity is associated with a higher energy range. The X-radiation is detected using first and second detector arrays 212, as described above. A first detector array 212 is arranged for detection of the first intensity associated with the lower energy range and comprises a plurality of X-radiation sensors 210, each of which comprises a pixel X-radiation sensor 210 which in one embodiment is a scintillator and a photodiode. As described above, accurate compositional analysis is enhanced when information from at least 10 pixels per particle is obtained. Accordingly, pixel size assists to determine minimum ore particle size in the range for material to be processed by the apparatus 200. Each scintillator generates light in response to absorbed X-radiation and the photodiode provides an electrical signal in response to the generated light. The electrical signal is then directed to a processor 214 for processing. As described above, a second detector array 212 is arranged for detection of the second intensities that are associated with the higher energy range and functions in the same manner as the first detector array 212. As described above, suitable filters and positioning of the first and second detector arrays 212 relative to each other enable separation of the first and second intensities that are detected by the detector arrays 212.

With further reference to FIG. 1, the method 100 further includes a step 106 of calculating a value that is indicative of a compositional property of the material, for example, the concentration of elemental iron in an iron ore particle, which is indicative of the grade of the iron ore.

Calculating of the value involves performing numerical operations using data associated with the detected first and second intensities. For determining the concentration of elemental iron, the compositional value is a "dual energy" value DE and is calculated so that the value DE is largely independent of non-compositional parameters of the particle such as thickness and porosity.

In this embodiment the value DE is calculated using equation 1, and is the value of the ratio, $$DE = \frac{\ln\left(\frac{I_1}{I_{0_1}}\right) + b}{\ln\left(\frac{I_2}{I_{0_2}}\right)^k} \qquad \text{Eq. 1}$$

where $I_1$ is the detected first intensity associated with the lower energy range and $I_2$ is the detected second intensity that is associated with the higher energy range. The intensity $I_{0_1}$ and $I_{0_2}$ are indicative of an intensity of the x-radiation in the respective higher and lower energy ranges to which the material is exposed.

The constants k and b are selected so that the calculated value DE is largely independent of non-compositional parameters.

The constants k and b are obtained empirically. By way of example of such empirical determination, the applicant first prepared standard samples with a known thickness and iron grade. Approximately 170 synthetic standards were manufactured by pressing ground samples of high and low grade iron ore into pellets. Using various combinations of high and low grade material a whole range of different grades, from 10% Fe to 65% Fe were made. Three thicknesses were manufactured, 5 mm, 10 mm, and 15 mm. The pellets were designed so that two 10 mm standards could be stacked to form a 20 mm standard, and similarly 15 mm standards could be stacked to give 30 mm standards. A suite of x-radiation measurements were taken of the standards. For each standard, logarithms of the average high and low energy absorptions were recorded. As indicated above, the dual energy analysis technique involves combining the low and high energy measurements according to Eq 1. Eq 1 is designed so that the dual energy value can be made independent of the sample thickness. To empirically find the best k and b values, standards of the same grade (but varying thickness) were grouped together, and the k and b values were adjusted until their dual energy values were as similar as possible. A final step involved using the DE data for each standard (generated using k and b) as well as the known iron grades and fit a curve relating DE to iron grade.

Figure 4:
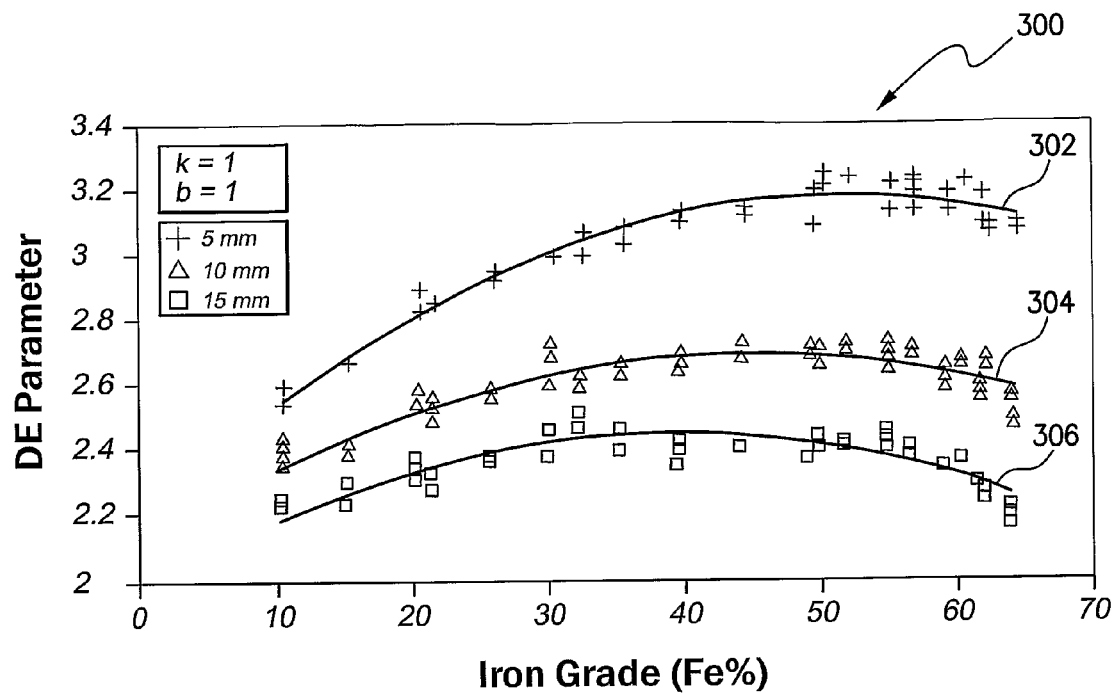
FIG. 4 is a plot of data showing the influence of a non-compositional parameter, namely thickness, on calculations for determining a value "DE" that is indicative of concentration determinations for iron concentration in particles of iron ore.

By way of further explanation, FIG. 4 shows a plot of calculated values of DE as a function of iron grade for k=1 and b=0. The plot 300 shows a first group 302 of data points that correspond to materials having an average thickness of 5 mm, a second group of data points corresponding to materials having an average thickness of 10 mm and a third group of data points corresponding to materials having an average thickness of 15 mm. As can be seen from FIG. 4, the calculated values DE are different for different thickness.

Figure 5:
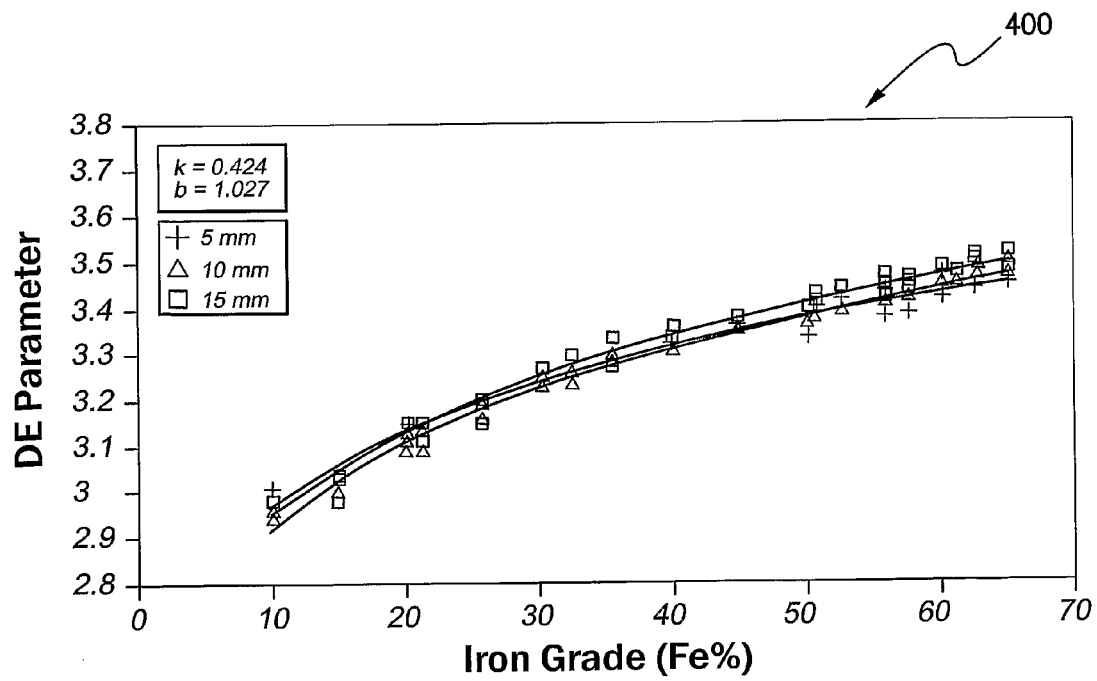
FIG. 5 is a plot of the same data in FIG. 4 with two constants selected in accordance with the invention for reducing the influence of thickness on calculations for determining a value "DE" that is indicative of iron concentration in iron ore.

FIG. 5 shows a plot of corrected values DE as a function of iron grade. The DE values were corrected by changing the values of the constants k and b in a manner such that the groups of data points 302, 304 and 306 were shifted to positions along substantially one curve. This was achieved for k=0.424 and b=1.027. Incorporating the constants k and b into equation 1 enables a value DE to be calculated that is indicative of an iron grade and that is largely independent of thickness of particles of the iron ore.

Figure 6:
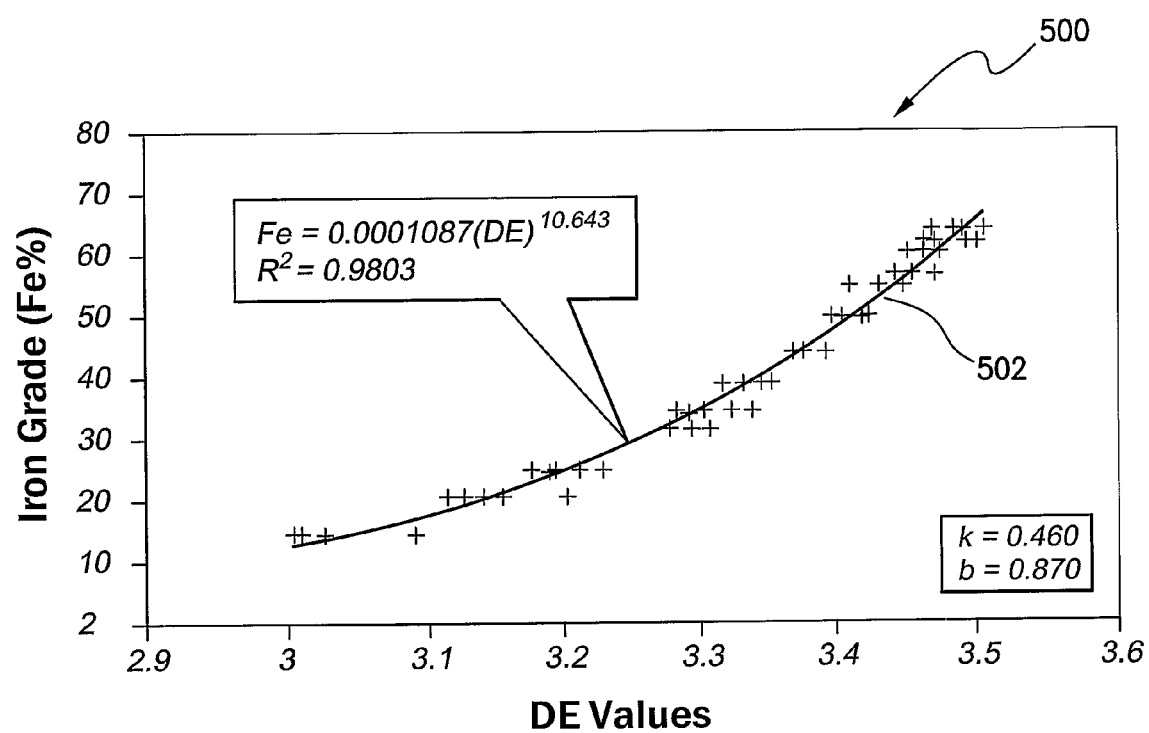
FIG. 6 shows data that was obtained using an embodiment of a method for analysing a composition of iron ore particles according to the invention by using predetermined constants k and b.

FIG. 6 shows a plot 500 of iron grade as a function of the calculated values DE. The plot shows a number of data points, each of which is associated with empirically determined constants k and b. Curve fitting procedures were then used to fit a curve 502 to the data points. The fitted curve 502 and a variation of equation 1 were then used to calculate fitted values for the constants of k and b. In this example the fitted value for the constant k is 0.460 and the fitted value for the constant b is 0.780. These fitted constants k and b can then be incorporated into the equation 1, which further improves the accuracy of compositional information derived from the value DE.

The processor 214 of the apparatus 200 is loaded with a computer program. An output of the arrays 212 is directed to the processor 214 and a computer program is arranged for instructing the processor 214 to calculate the value DE in the above-described manner.

It is to be appreciated by a person skilled in the art that the invention may take many different forms to the embodiments described in relation to the Figures. For example, the radiation may be generated and detected in any other suitable way. Further, the source of radiation may be a source of γ-radiation rather than x-radiation. In addition, any other suitable material, also including liquids, may be analysed by the method and apparatus in accordance with embodiments of the present invention. Specifically, the invention is not limited to analyzing iron-containing ores. There are specific references to other materials, namely, copper-containing and nickel-containing ores and coal, in the above description. The invention extends to any other suitable materials. It is also to be appreciated that the value that is indicative of a compositional property of the material may alternatively be calculated using a suitable equation other than equation 1.

Prior art mentioned in the specification is not to be, and should not be, taken as an admission that the prior art forms part of the common general knowledge of a skilled person in Australia or any other jurisdiction.

It will be understood that the term "comprises" or its grammatical variants as used in the specification and claims is equivalent to the term "includes" and is not to be taken as excluding the presence of other features or elements.

The invention claimed is:

1. A method of analysing particles of ore which include a constituent, the method comprising the steps of:
   (a) exposing particles of the ore to x-radiation having a range of x-radiation energies from a source of x-radiation;
   (b) detecting x-radiation intensities with a detector for detecting x-ray radiation intensities at two different energy levels or at two different ranges of energies transmitted through the particles; and
   (c) determining the concentration of the constituent occurring in particles from the respective detected intensities by calculating a value (DE) indicative of the concentration of the constituent by calculating a ratio of first and second quantities related to detected first and second radiation intensities associated with first and second energy levels or first and second energy ranges and using at least one constant, and with at least one constant being selected so that an influence of thickness of the ore on the calculated value is reduced.

2. The method defined in claim 1 wherein step (a) of exposing the material to radiation comprises operating the x-radiation source at a voltage of 50 kV to 400 kV.

3. The method defined in claim 1 wherein step (b) of detecting x-radiation intensities comprises detecting x-radiation intensities in two different, non-overlapping ranges of energies.

4. The method defined in claim 1 comprises selecting the at least one constant so that the calculated concentration is largely independent of the non-compositional parameters of the material.

5. The method defined in claim 1 wherein calculating the value comprises calculating a ratio of a first quantity that is a function of a detected first intensity $I_1$ associated with the first energy level or first energy range and a second quantity that is a function of a detected second intensity $I_2$ associated with the second energy level or second energy range.

6. The method defined in claim 1 wherein calculating the value comprises calculating the ratio:

$$\frac{\ln\left(\frac{I_1}{I_{0_1}}\right)+b}{\ln\left(\frac{I_2}{I_{0_2}}\right)^k} \qquad \text{Eq. 1}$$

where k is a first constant that is selected so that an influence of thickness of the ore on the calculated value is reduced, b is a second constant that is selected so that an influence of thickness of the ore on the calculated value is reduced and $I_1$ is a first detected x-radiation intensity at a first energy level or energy range, $I_2$ is a second detected x-radiation intensity at a second energy level or second range, $I_{O_1}$ is indicative of the x-radiation intensity of the first energy level or energy range to which the ore is exposed and $I_{O_2}$ is indicative of a radiation intensity of the second energy level or energy range to which the ore is exposed.

7. The method defined in claim 1 comprises determining the at least one constant empirically by analyzing thickness and porosity dependency of the first and second intensities for ores with different known grades.

8. The method defined in claim 1 comprises determining the at least one constant by numerical operations of displayed data.

9. The method defined in claim 1 wherein step (b) of detecting x-radiation intensities at two different energy levels or energy ranges comprises making multiple measurements of intensities of transmitted x-radiation through each particle.

10. The method defined in claim 1 wherein step (b) of detecting x-radiation intensities at two different energy levels or energy ranges comprises making multiple measurements along the length and across the width of each particle of intensities of x-radiation transmitted through each particle; and step (c) of determining the concentration of the constituent further comprises averaging measurements in step (b) to determine and average concentration for each particle.

11. The method defined in claim 1 wherein step (a) of exposing particles to x-radiation comprises conveying the particles at at least 5 m/s through a beam of x-radiation.

12. The method defined in claim 1 wherein step (a) of exposing particles to x-radiation comprises conveying the particles at a through-put of at least 100 tonnes per hour (tph).

13. The method defined in claim 1 further comprising step (d) sorting the particles based on the concentration of the constituent occurring in particles.

14. An apparatus for analysing particles of an ore which includes a constituent comprises:
   (a) a source of x-radiation for producing a beam of x-radiation in at least first and second energy levels or first and second energy ranges;
   (b) a detector for detecting x-radiation produced by the source of x-radiation, wherein the detector comprises two arrays of x-radiation sensors with each array being configured to detect x-radiation of a different energy level or different energy range, wherein each array of x-radiation sensors is positioned such that in use the same x-radiation beam that passes through the particle impinges on the corresponding x-radiation sensors in each array;

conveying means for conveying particles of the ore relative to the source of x-radiation such that the particles pass between the source of x-radiation and the detector; and means for determining the concentration of the constituent in each particle from the detected x-radiation at the first and second energy levels or the first and second ranges of energies; and wherein the means for determining concentration comprises a means for calculating a value indicative of the concentration of the constituent from detected radiation intensities to obtain information concerning the composition of the ore, the detected radiation intensities being first and second intensities of radiation that are transmitted through the ore and being associated with respective first and second energy levels or first and second ranges of energies, and the means for calculating the value is further configured to perform a numerical operation using at least one constant selected so that an influence of non-compositional parameters of the ore on the calculated value is reduced.

15. The apparatus defined in claim 14 wherein the concentration determining means is adapted to determine the concentration by calculating a value from x-radiation intensities detected by the detector.

16. The apparatus defined in claim 14 wherein the detector further comprises two filters respectively located between the x-radiation source and the arrays of x-radiation sensors, and with the filters being adapted to enable transmission of x-radiation of different levels of energy or different ranges of energies to the respective arrays.

* * * * *